(12) United States Patent
Loehn et al.

(10) Patent No.: US 7,858,328 B2
(45) Date of Patent: Dec. 28, 2010

(54) HIGH-THROUGHPUT ENZYME-LINKED IMMUNO ABSORBENT ASSAY (ELISA) FOR DETERMINATION OF RHO-KINASE (ROK) ACTIVITY

(75) Inventors: Matthias Loehn, Kelkheim (DE); Yuri Ivashchenko, Hattersheim (DE); Elke Kessler, Hanau (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 573 days.

(21) Appl. No.: 11/720,353

(22) PCT Filed: Dec. 7, 2005

(86) PCT No.: PCT/EP2005/013088

§ 371 (c)(1),
(2), (4) Date: Apr. 3, 2008

(87) PCT Pub. No.: WO2006/063723

PCT Pub. Date: Jun. 22, 2006

(65) Prior Publication Data

US 2009/0017478 A1    Jan. 15, 2009

(30) Foreign Application Priority Data

Dec. 16, 2004    (EP) .................................. 04029769

(51) Int. Cl.
*G01N 33/53* (2006.01)
*G01N 31/00* (2006.01)

(52) U.S. Cl. .......................... 435/7.21; 435/7.1; 436/1; 436/501; 436/518; 424/9.1; 424/520; 422/1; 422/50; 530/300; 530/350

(58) Field of Classification Search ................ None
See application file for complete search history.

(56) References Cited

U.S. PATENT DOCUMENTS 5,906,819 A    5/1999 Kaibuchi et al.
2003/0232391 A1   12/2003 Prescott et al.

FOREIGN PATENT DOCUMENTS

EP    1096014 A2    5/2001
WO    WO 2004/035811 A2    4/2004

OTHER PUBLICATIONS

Mutsuki et al., The COOH terminus of Rho-kinase negatively regulates Rho-Kinase activity, J. of Biological Chemistry, vol. 274, No. 45, Nov. 5, 1999, pp. 32418-32424.
Turner et al., Characterization and purification of truncated human Rho-kinase II expressed in Sf-21 cells, Archives of Biochemistry and Biophysics, vol. 405, No. 1, Sep. 1, 2002, pp. 13-20.
BD Transduction Laboratories, Purified Mouse Anti-Phosphoserine/threonine, Technical Data Sheet.
Becton Dickinson France, Ser, Thr, Tyr Phosphorylation Detection, http://www.bdeurope.com/cgi-bin/bdweb/eservices/catalog, accessed Nov. 2, 2009.
Chernyavsky et al., Central Role of Alpha9 Acetylcholine Receptor in Coordinating Keratinocyte Adhesion and Motility At The Initiation of Epithelialization, Exp. Cell Res. vol. 313, No. 16, Oct. 1, 2007.
Collins et al., Epigallocatechin-3-gallate (EGCG), A Green Tea Polyphenol, Suppresses Hepatic Gluconeogenesis through 5'-AMP-activated Protein Kinase, J. of Biol. Chem., vol, 282, No. 41, pp. 30143-30149.
Kim et al., PKC-dependent functional switch of rpS3 between translation and DNA repair, Biochimica et Biophysicsa Acta, 2009, pp. 395-405.
Liao et al., The P2Y2 nucleotide receptor requires interaction with alpha v integrins to access and activate G12, Journal of Cell Science, vol. 120, No. 9, 2007, pp. 1654-1562.
Paik et al., Sphingosine 1-phosphate receptor regulation of N-cadherin mediates vascular stabilization, Genes & Development, vol. 18, 2004, pp. 2392-2403.
Riento et al., Rocks: Multifunctional Kinases in Cell Behavior, Nature, vol. 4, 2003, Jun. 2003, pp. 446-456.
Roche, PhosSTOp, Phosphatase inhibitor Cocktail Tablets provided in EASYpacks, Cat. No. 04 906 845 001 and Cat No. 04 906 837 001, Version Oct. 2006.
Sanchez et at., PTEN as an effector in the signaling of antimigratory G protein-coupled receptor, PNAS, vol. 102, No. 12, Mar. 22, 2005, pp. 4312-4317.
Tanimoto et al., Down-regulation of BiP/GRP78 sensitizes resistant prostate cancer cells to gene-therapeutic overexpression of REIC/Dkk-3, International Journal of Cancer, published on-line, Jul. 22, 2009.
Tawar et al., Renal Phosphodiesterase 4B Is Activated in the Dahl Salt-Sensitive Rat, Hypertension, Mar. 2008, pp. 762-766.
Yamaguchi et al., Activating Transcription Factor 3 and Early Growth Response 1Are the Novel Targets of LY294002 in a Phosphatidylinositol 3-Kinase-Independent Pathway , Cancer Res 2006, vol 66, No. 4, Feb. 15, 2006, pp. 2376-2384.
Yan et al., Protein phosphorylation: technologies for the identification of phosphoamino acids, J. of Chromatography, vol. 808, 1998, pp. 23-41.

*Primary Examiner*—Lisa V Cook

(57) ABSTRACT

The invention is referring to an assay for measuring the activity of a ROK (Rho kinase) protein by means of a biotinylated peptide.

19 Claims, 4 Drawing Sheets

GGG AKRRRL SSLRASTS

Fig. 3

| Inhibitor Conc(nM) 31 | Inhibitor Conc(nM) 93 | Inhibitor Conc(nM) 278 | Inhibitor Conc(nM) 833 | Inhibitor Conc(nM) 2500 | Inhibitor Conc(nM) 7500 | Mean IC50(nM) |
|---|---|---|---|---|---|---|
| -6.28 | -2.23 | 14.18 | 44.49 | 73.21 | 92.97 | 1072.78 |
| -5.66 | -2.08 | 15.49 | 67.03 | 92.34 | 99.36 | 611.09 |
| -5.65 | -0.63 | 12.04 | 47.19 | 82.68 | 97.71 | 915.07 |
| -1.94 | 4.87 | 28.33 | 71.34 | 92.82 | 99.36 | 488.17 |
| 2.55 | 6.89 | 27.40 | 73.84 | 92.57 | 98.79 | 473.71 |
| -3.35 | 9.74 | 22.10 | 58.30 | 87.63 | 97.91 | 651.39 |
| -9.44 | -1.30 | -1.89 | -2.09 | 7.05 | 19.00 | >7500 |
| -3.01 | 3.21 | -3.59 | 9.65 | 42.27 | 80.21 | 3102.74 |
| -2.67 | -0.88 | 6.98 | -0.34 | 14.15 | 49.75 | >7500 |
| 2.22 | -0.01 | 16.33 | 52.76 | 80.48 | 98.50 | 821.89 |
| -5.40 | 5.52 | 17.06 | 56.63 | 86.46 | 98.81 | 721.48 |
| 4.73 | -2.95 | 3.33 | 31.75 | 71.89 | 89.82 | 1416.43 |
| -9.54 | 3.02 | 0.78 | 12.02 | 40.83 | 75.41 | 3324.44 |
| -0.81 | -1.86 | 9.36 | 35.66 | 73.97 | 95.48 | 1238.45 |
| -6.64 | -1.73 | -3.24 | 5.99 | 33.90 | 67.96 | 4281.67 |
| -3.53 | 13.96 | 38.53 | 79.58 | 95.74 | 99.84 | 360.12 | though

HIGH-THROUGHPUT ENZYME-LINKED IMMUNO ABSORBENT ASSAY (ELISA) FOR DETERMINATION OF RHO-KINASE (ROK) ACTIVITY

This application claims priority to International application number PCT/EP05/013088, filed Dec. 7, 2005 and foreign application number EP 04029769.9 filed Dec. 16, 2004.

The invention is referring to an assay for measuring the activity of a ROK (Rho kinase) protein by means of a biotinylated peptide.

The invention pertains to an assay for identification of a compound that modulates (stimulates, diminishes, maintains) the activity of ROK protein wherein a] a peptide that is capable of being phosphorylated by ROK protein is provided;
b] ROK protein is provided;
c] an antibody that is capable of recognizing the peptide from a] if this peptide is phosphorylated, is provided;
d] a chemical compound is provided;
e] the peptide from a] is incubated with the ROK protein from b] as well as with the chemical compound from d] under conditions that allow phosphorylation of the peptide;
f] the antibody from c] is used after the incubation performed according to e] has been finished to detect phosphorylation of the peptide;
g] the result from f] is possibly compared to the result from an experiment wherein incubation of the peptide from a] the ROK protein from b] is performed without having chemical compound according to d] present.

Such an assay can easily be carried out in ELISA or RIA (Radio Immun Assay) format.

The peptide of step a] with respect to the assay as depicted before can consist of a size of between 15 to 25 amino acids. This peptide can comprise or consist of the following amino acid sequence: GGGGAKRRRLSSLRASTS. The peptide according to step a] of the assay can be used in a chemically modified form as e.g. being biotinylated or linked to a DNA or antibody.

The ROK protein of step b] with respect to the assay as depicted before can comprise the amino acid sequence of the according human protein or can be derived or taken from human biological material. Such a ROK protein can be manufactured by different techniques as e.g. by a procedure having biological material or processing steps of recombinant nature included. The assay of the invention as disclosed before can e.g. be used for a High Throughput Screening of a compound that modulates the activity of ROK protein.

The invention pertains also to a kit of parts comprising of
a] a peptide that is able of being phosphorylated by ROK protein;
b] ROK protein;
c] an antibody that is capable of recognizing the peptide from a] if this peptide is phosphorylated;
d] possibly a second antibody that is capable of recognizing the antibody from c] and/or is linked to a marker system (e.g. alkaline phosphatase, β-glucuronidase, peroxidase, other enzyme);
e] possibly reagents, buffers and/or equipment for realizing phosphorylation of the peptide from a] and/or a ELISA set up.

The peptide of step a] with respect to the kit of parts as mentioned before consists of a size of between 15 to 25 amino acids. This peptide can comprise or consist of the following amino acid sequence: GGGGAKRRRLSSLRASTS. The peptide according to step a] of the assay can be used in a chemically modified form as e.g. being biotinylated or linked to a DNA or an antibody. The ROK protein of step b] with respect to the assay as depicted before can comprise the amino acid sequence of the according human protein or can be derived or taken from human biological material. Such a ROK protein can be manufactured by different techniques as e.g. by a procedure having biological material or processing steps of recombinant nature included.

The invention pertains further to the manufacturing of a kits of parts as mentioned before wherein a] a peptide that is capable of being phosphorylated by ROK protein is provided;
b] ROK protein is provided;
c] an antibody that is capable of recognizing the peptide from a] if this peptide is phosphorylated is provided;
d] possibly a second antibody that is capable of recognizing the antibody from c] and/or is linked to a marker system (e.g. alkaline phosphatase, β-glucuronidase, peroxidase, other enzyme) is provided;
e] possibly reagents, buffers and/or equipment for realizing the phosphorylation of the peptide from a] and/or a ELISA set up are provided;
f] the components from a] to e] are packages accordingly and combined with a protocol mentioning therein amongst other the components of the kit of parts as well as the procedural steps of the resulting ROK protein assay.

The kit of parts as mentioned before can be used e.g. for determining the activity of a ROK protein, or for identifying of a compound that modulates the activity of a ROK protein, or for High-Throughput Screening.

The invention pertains further to a peptide comprising or consisting of the following amino acid sequence: GGG-GAKRRRLSSLRASTS. Such a peptide can be chemically modified as e.g. biotinylated. The invention pertains also to the use of such a peptide for measuring the activity of a ROK protein.

A chemical compound in context of this invention shall mean any organic and/or carbohydratic compound that is either produced by chemical synthesis or isolated from a natural source. Such a compound may have a molecular weight of between 50 and 50 000 Dalton.

A protein shall be regarded as functional in context of this invention when it is in a condition to perform an activity in a biological context in particular as part of a living cell. Such an activity is detectable e.g. by an assay. A transporter is functional for example when this transporter moves a compound in particular the transporter's biological substrate from outside a cell into the inner compartment of this cell or vice versa. A biological substrate of an ion transporter protein consists e.g. of a monovalent and/or a divalent ion or other ions. The substrate of a glucose transporter protein is e.g. glucose. The substrate of a multiple drug resistance protein is e.g. a drug alone or conjugated to glutathione or gluconate.

The handling of proteins in context of this invention can be achieved by a person skilled in the art applying the according protocols from "Current Protocols in Protein Science" published by John Wiley & Sons (edited by: John E. Coligan, Ben M. Dunn, Hidde L., Ploegh, David W. Speicher, Paul T. Wingfield; 0-471-11184-8-Looseleaf; 0-471-14098-8-CDROM).

The handling of techniques concerning Molecular Biology as e.g. cloning, transforming of cells, sequencing, modifying promoters, expression proteins or others can be achieved a the person skilled in the art by applying the according protocols from "Current Protocols in Molecular Biology" published by John Wiley & Sons (edited by: Fred M. Ausubel, Roger Brent, Robert E. Kingston, David D. Moore, J. G. Seidman, John A. Smith, Kevin Struhl; 0-471-50338-X-Looseleaf; 0-471-306614CDROM).

Biological material means any material containing genetic information and capable of reproducing itself or being reproduced in a biological system. Recombinant biological material is any biological material that was produced, has been changed or modified by means of recombinant techniques. Recombinant techniques are defined in textbooks as e.g. "Current Protocols in Molecular Biology, published by John Wiley & Sons; ISBN: 0471-50338-X-Looseleaf or 0-471-30661-4-CD-ROM".

The handling of biological cells can be achieved a the person skilled in the art by applying the according protocols from "Current Protocols in Cell Biology" published by John Wiley & Sons (edited by: Juan S. Bonifacino, Mary Dasso, Jennifer Lippincott-Schwartz, Joe B. Harford, Kenneth M. Yamada; 0-471-24108-3-Looseleaf; 0-471-24105-9-CDROM).

EXAMPLES

Rho-kinase (ROK) represents a highly validated target for cardiovascular diseases. Therefore, the search for specific ROK-inhibitors is the focus of many groups working in cardiovascular area. Here, we describe the development of an ELISA, specific for ROK-activity. The ROK-ELISA detects the amount of a ROK-phosphorylated peptide. ROK-Inhibitors inhibit ROK-activity and reduce thereby the amount of ROK-mediated peptide phosphorylation. ROK-ELISA was developed in a medium throughput 96-well format as well as in a high throughput 384-well format.

Protocol:

Stock Solutions:

Biotinylated S6 peptide: store at −20° C. in aliquots of 1 ml in Tris buffer 25 mM pH 8.0 (5 mg/ml)

recombinant active ROK: store at −20° C. in aliquots of 10 μl (1 mg/ml)

| ATP | 100 mM | Sigma Cat.# A-6419 Lo# 29H7051 | −20° C. |
|---|---|---|---|
| Stop solution | 3 N HCL | Hydrochloride standard solution (Sigma) | RT |
| $MgCL_2$ | 1 M | $MgCl_2$ (Sigma) | RT |
| BSA | 10% | Sigma | −20° C. |
| DTT | 1 M | Sigma | −20° C. |
| ODP-Peroxidase Substrate | | Sigma | 2-8° C. |
| Superblock buffer | +0.2% TWEEN 20 | Superblock (Blocking buffer in TBS; Pierce Cat.# 37535), TWEEN 20 | 2-8° C. |
| washing buffer (PBS) | PBS 1 × +0.2% TWEEN 20 | PBS w/o $CaCl_2$ and $MgCl_2$, Gibco # 2006-01, TWEEN 20 | 2-8° C. |
| reaction buffer | 25 mM Tris pH 7.4; 0.02% BSA; 2 mM DTT | | use freshly prepared only |

1) Coating of streptavidin coated wells with the biotinylated S6 peptide 0.5 ng/well for 2 hours or overnight at room temperature
2) triple wash out of excess S6 peptide with PBS 100 μl/well
3) Preparation of a 10×ATP solution in the desired concentration in reaction buffer with $MgCl_2$ on ice
4) Dilute ROK in reaction buffer on ice, final concentration: 10 ng/well
5) Prepare a 10× substance solution in the desired concentration ROK-ELISA 96-well format Total volume=100 μl 1) Preincubation of inhibitors (10 μl of a 10× concentrated solution) in the desired final concentrations with 80 μl of ROK for 10 minutes
2) add 10 μl ATP of a 10× concentrated ATP solution in the desired final concentration
3) incubate the plate for one hour at 30° C.
4) Stop kinase reaction with 100 μl of a 500 mM EDTA solution
5) remove supernatant of all wells
6) add 100 μl/well of primary monoclonal phosphospecific antibody (1:1000) and incubate for 15 minutes at room temperature
7) add 100 μl/well of secondary antibody (1:2000) and incubate for one hour at room temperature
8) remove supernatant and wash five times with PBS 200 μl/well
9) add 100 μl of substrate solution to all wells and incubate for 10 minutes at room temperature
10) add 100 μl stop solution to all wells
11) measure OD at 492 nm ROK-ELISA 384-well format Total volume=10 μl 1) Preincubation of inhibitors (1 μl of a 10× concentrated solution) in the desired final concentrations with 8 μl of ROK for 10 minutes
2) add 1 μl ATP of a 10× concentrated ATP solution in the desired final concentration
3) incubate the plate for one hour at 30° C.
4) Stop kinase reaction with 10 μl of a 500 mM EDTA solution
5) remove supernatant of all wells
6) add 10 μl/well of primary monoclonal phosphospecific antibody (1:1000) and incubate for 15 minutes at room temperature
7) add 100 μl/well of secondary antibody (1:2000) and incubate for one hour at room temperature
8) remove supernatant and wash five times with PBS 30 μl/well
9) add 10 μl of substrate solution to all wells and incubate for 10 minutes at room temperature
10) add 10 μl stop solution to all wells
11) measure OD at 492 nm.

Material

ROK (ROKα/ROCK-II (active recombinant aa 11-550 or longer),

Biotinylated S6 peptide (Biotin-GGGGARRRLSSL-RASTS),

Streptavidin coated 96- or 384-well plates (e.g. Roche StreptaWell, High Bind (transparent) 1989685/1989677, Roche Diagnostics, Mannheim), Monoclonal phosphospecific antibody from Transduction Labs (clone 22a, BD Biosciences, Heidelberg), goat-anti-mouse IgG-HRP 200 μg/0.5 ml (Santa Cruz Cat# sc-2005).

DESCRIPTION OF FIGURES

FIGS. 3 and 4A and B illustrate results (% inhibition and IC50 calculation) from the ROK ELISA

---

SEQUENCE LISTING

Figures 1, 2:
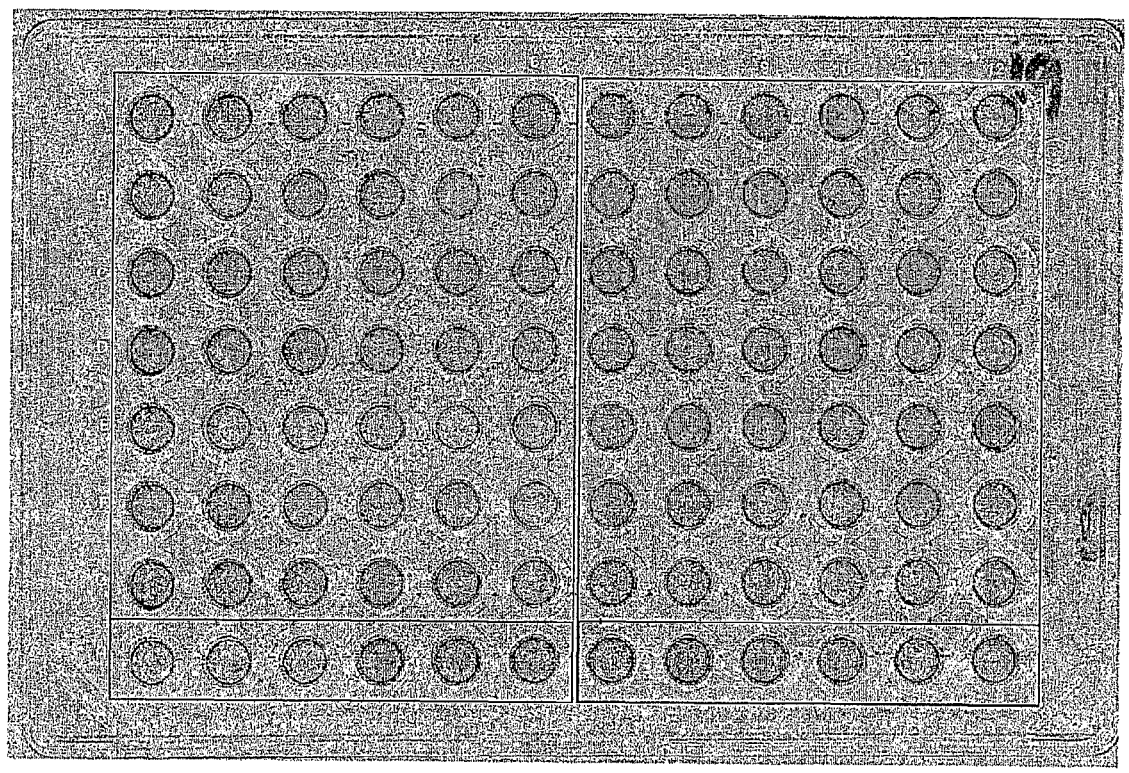
FIG. 1 depicts the amino acid sequence according to SEQ ID NO. 1.
FIG. 2 represents a typical layout for the ROK ELISA Row H 1-6 serves as control wells for kinase reaction. Wells of row H1-3 were without kinase and with ATP and represent the minimal signal. Wells of row H4-6 were with kinase and with ATP and represent the maximal signal. Wells of row H7-12 served for a concentration relationship for the reference compound. All other wells were used to obtain a concentration relationship for the compound of interest. Please note the pale color in wells of row E1-7 indicating that a highly potent inhibitor inhibited ROK mediated substrate phosphorylation over the whole concentration range used. In the case of IC50 estimation with single point determination at the same time 14 compounds plus one reference compound can be tested in the 96-well format.
Figure 4:
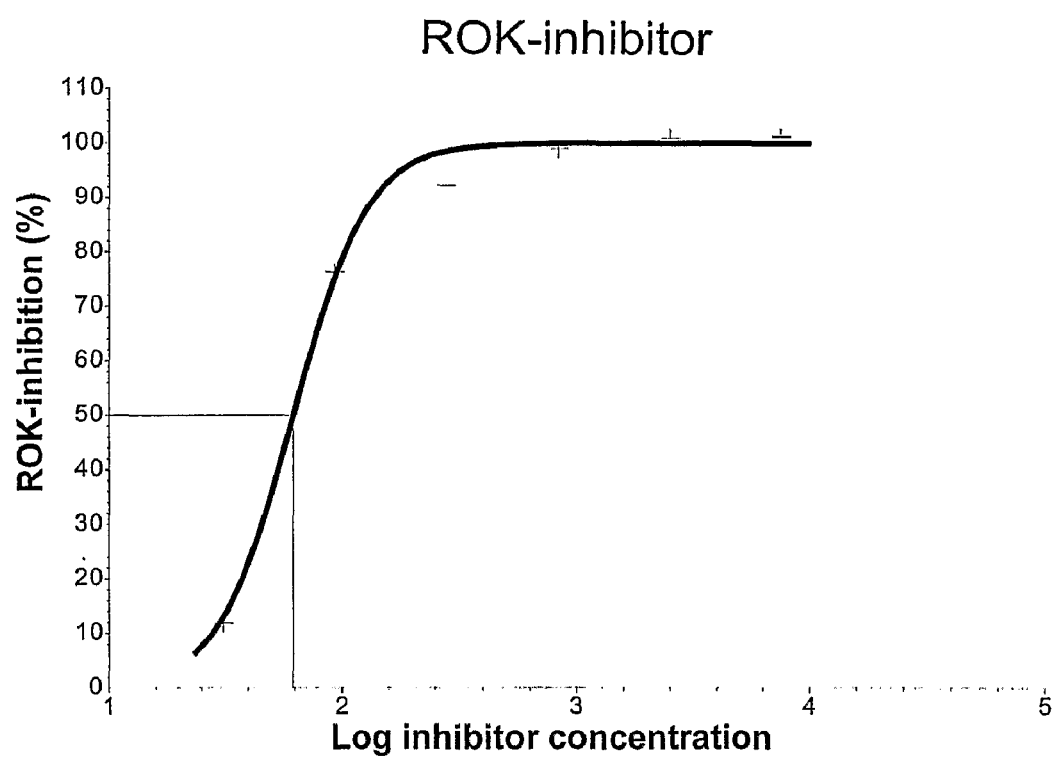
Figure 4:
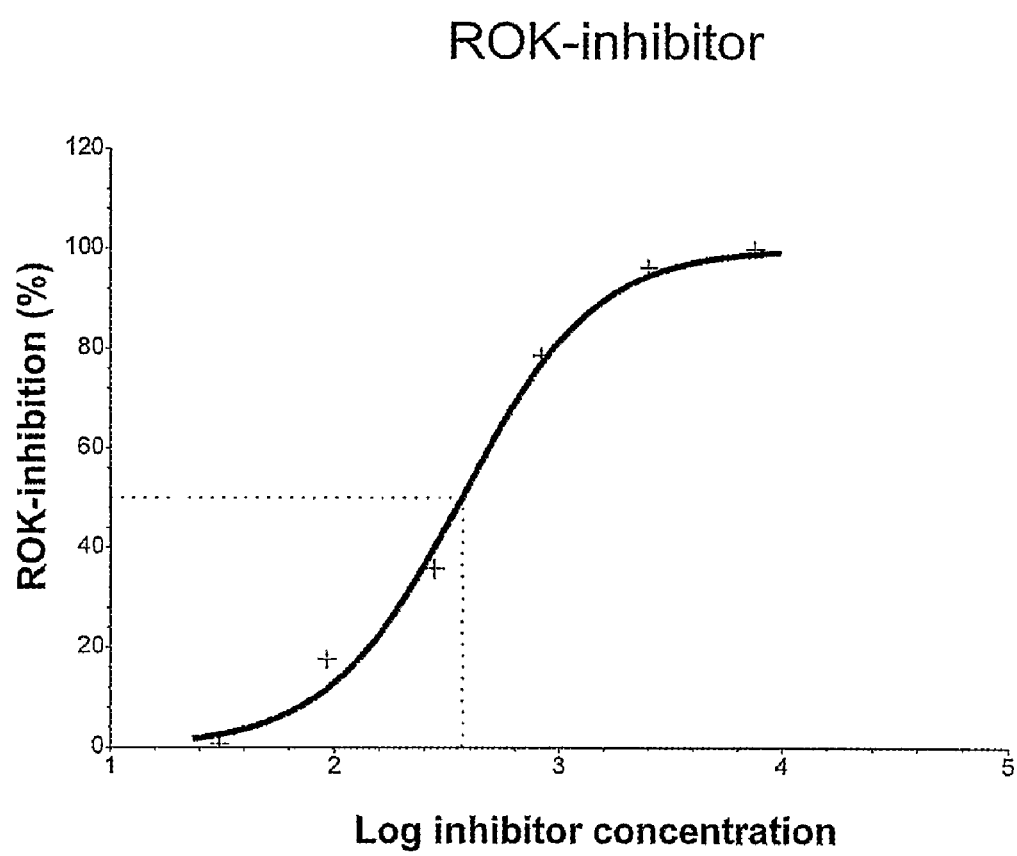

```
<160> NUMBER OF SEQ ID NOS: 1

<210> SEQ ID NO 1
<211> LENGTH: 18
<212> TYPE: PRT
<213> ORGANISM: Artificial Sequence
<220> FEATURE:
<223> OTHER INFORMATION: peptide capable of being phosphorylated by ROK

<400> SEQUENCE: 1

Gly Gly Gly Gly Ala Lys Arg Arg Arg Leu Ser Ser Leu Arg Ala Ser
1               5                   10                  15

Thr Ser
```

---

The invention claimed is:

1. An assay for identifying a compound that modulates the activity of ROK protein comprising the steps of
    i) providing a peptide capable of being phosphorylated by ROK protein,
    ii) providing a ROK protein,
    iii) providing a chemical compound,
    iv) incubating said peptide with said ROK protein and said chemical compound under conditions that allow phosphorylation of said peptide,
    v) adding an antibody capable of recognizing said peptide when said peptide is phosphorylated after incubation is completed to detect phosphorylation of said peptide,
    vi) comparing the results in step v) with results when incubation of said peptide and said ROK protein is performed without the presence of said chemical compound.

2. The assay according to claim 1 wherein said incubation is performed as an ELISA assay.

3. The assay according to claim 1 wherein said incubation is performed as an RIA assay.

4. The assay according to claim 1 wherein said peptide has a size of 15 to 25 amino acids.

5. The assay according to claim 4 wherein said peptide has the amino acid sequence consisting of GGGGAKRRRLSS-LRASTS SEQ ID NO:1.

6. The assay according to claim 4 or 5 wherein said peptide is biotinylated.

7. The assay according to claim 1 wherein said ROK protein is from human.

8. The assay according to claim 7 wherein said ROK protein has been manufactured recombinantly.

9. The assay according to claim 1 wherein said is a high-throughput screen.

10. A kit comprising the parts of
    i) a peptide capable of being phosphorylated by a ROK protein;
    ii) a ROK protein;
    iii) an antibody capable of recognizing said peptide when it is phosphorylated.

11. The kit according to claim 10 which additionally comprises a second antibody capable of recognizing said antibody capable of recognizing said protein.

12. The kit according to claim 10 or 11 which additionally comprises reagents and buffers for realizing phosphorylation of said peptide.

13. The kit according to claim 10 wherein said peptide has a size of 15 to 25 amino acids.

14. The kit according to claim 13 wherein said peptide has the amino acid sequence consisting of GGGGAKRRRLSS-LRASTS SEQ ID NO:1.

15. The kit according to claim 10 wherein said peptide is biotinylated.

16. The kit according to claim 10 wherein said ROK protein is from human.

17. The kit according to claim 10 wherein said ROK protein has been manufactured recombinantly.

18. A peptide consisting of the amino acid sequence GGG-GAKRRRLSSLRASTS SEQ ID NO:1.

19. The peptide according to claim 18 wherein said peptide is biotinylated.

* * * * *

UNITED STATES PATENT AND TRADEMARK OFFICE
CERTIFICATE OF CORRECTION

| | | |
|---|---|---|
| PATENT NO. | : 7,858,328 B2 | Page 1 of 1 |
| APPLICATION NO. | : 11/720353 | |
| DATED | : December 28, 2010 | |
| INVENTOR(S) | : Matthias Loehn et al. | |

It is certified that error appears in the above-identified patent and that said Letters Patent is hereby corrected as shown below:

On the first page, in field (56), in column 2, under "Other Publications", line 20, delete "Biophysicsa" and insert -- Biophysica --, therefor.

On the first page, in field (56), in column 2, under "Other Publications", line 24, delete "1562." and insert -- 1662. --, therefor.

On the first page, in field (56), in column 2, under "Other Publications", line 43, delete "1Are" and insert -- 1 are --, therefor.

In column 2, line 59-60, delete "can be achieved a the person skilled" and insert -- can be achieved by a person skilled --, therefor.

In column 3, line 7-8, delete "can be achieved a the person skilled" and insert -- can be achieved by a person skilled --, therefor.

In column 6, line 11-12, in claim 9, delete "wherein said is a high-throughput screen" and insert -- wherein the said assay is a high-throughput screen --, therefor.

Signed and Sealed this
Twenty-second Day of March, 2011

David J. Kappos
*Director of the United States Patent and Trademark Office*